(12) United States Patent
Raimarckers et al.

(10) Patent No.: US 12,716,368 B2
(45) Date of Patent: Aug. 25, 2026

(54) MONITORING THE OIL OF A LUBRICATION DEVICE

(71) Applicant: SAFRAN AERO BOOSTERS SA, Herstal (BE)

(72) Inventors: Nicolas Oscar Louis Ghislain Raimarckers, Herstal (BE); Stephane Alain Luc Ghislain Bougelet, Herstal (BE)

(73) Assignee: SAFRAN AERO BOOSTERS SA, Herstal (BE)

( * ) Notice: Subject to any disclaimer, the term of this patent is extended or adjusted under 35 U.S.C. 154(b) by 0 days.

(21) Appl. No.: 17/919,166

(22) PCT Filed: Apr. 13, 2021

(86) PCT No.: PCT/EP2021/059575
§ 371 (c)(1),
(2) Date: Oct. 14, 2022

(87) PCT Pub. No.: WO2021/209456
PCT Pub. Date: Oct. 21, 2021

(65) Prior Publication Data

US 2023/0160322 A1 May 25, 2023

(30) Foreign Application Priority Data

Apr. 14, 2020 (BE) .................................. 2020/5244

(51) Int. Cl.
*F01D 25/20* (2006.01)
*B01D 21/26* (2006.01)
(Continued)

(52) U.S. Cl.
CPC .......... *F01D 25/20* (2013.01); *B01D 21/267* (2013.01); *F01D 21/003* (2013.01); *F01D 25/18* (2013.01); *F16N 29/00* (2013.01); *G01N 1/2035* (2013.01); *G01N 33/2858* (2013.01); *F05D 2260/606* (2013.01); *F05D 2260/607* (2013.01); *F05D 2260/609* (2013.01); *F05D 2270/804* (2013.01); *F16N 2200/04* (2013.01)

(58) Field of Classification Search
CPC .............. G01N 1/2035; G01N 33/2858; F05D 2260/606; F16N 29/00; F16N 2200/04; B01D 21/267
See application file for complete search history.

(56) References Cited

U.S. PATENT DOCUMENTS 5,028,318 A 7/1991 Aslin
6,348,087 B1 2/2002 Aslin
(Continued)

OTHER PUBLICATIONS

International Search Report for PCT App. No. PCT/EP2021/059575.

*Primary Examiner* — Minh Truong
(74) *Attorney, Agent, or Firm* — Sandberg Phoenix & von Gontard, P.C.

(57) ABSTRACT

A device for detecting particles in a lubricating oil of a machine, comprising a particle separator; at least one particle detector; a bypass conduit for the particle-concentrating oil, fluidly connected to an oil outlet of the particle separator, concentrating the particles; and wherein the at least one particle detector is operatively mounted on the bypass conduit so as to be able to detect particles in the bypass conduit.

15 Claims, 2 Drawing Sheets

(51) Int. Cl.

| | |
|---|---|
| ***F01D 21/00*** | (2006.01) |
| ***F01D 25/18*** | (2006.01) |
| ***F16N 29/00*** | (2006.01) |
| ***G01N 1/20*** | (2006.01) |
| ***G01N 33/28*** | (2006.01) |

(56) References Cited

U.S. PATENT DOCUMENTS

| | | | | |
|---|---|---|---|---|
| 7,288,139 | B1 | 10/2007 | Showalter | |
| 10,137,462 | B2 * | 11/2018 | Goulds | B04C 9/00 |
| 2006/0107837 | A1 * | 5/2006 | Showalter | B01D 19/0057 96/208 |
| 2009/0014245 | A1 * | 1/2009 | Shevchenko | F02C 7/06 73/112.01 |
| 2009/0183950 | A1 | 7/2009 | Brouillet | |
| 2010/0031754 | A1 * | 2/2010 | Atkinson | G01N 1/2035 73/861.04 |
| 2014/0009621 | A1 * | 1/2014 | Tucker | G01N 15/0227 348/159 |
| 2016/0370275 | A1 * | 12/2016 | Weiser | B03C 1/282 |
| 2017/0056894 | A1 | 3/2017 | Santeler | |
| 2021/0054763 | A1 * | 2/2021 | Kempers | B03C 1/286 |

* cited by examiner

MONITORING THE OIL OF A LUBRICATION DEVICE

CROSS-REFERENCE TO RELATED APPLICATIONS

The present invention is the U.S. national stage under 35 U.S.C. § 371 of International Application No. PCT/EP2021/059575 which was filed on Apr. 13, 2021, and which claims the priority of application BE 2020/5244 filed on Apr. 14, 2020 the contents of which (text, drawings and claims) are incorporated here by reference in its entirety.

FIELD

The invention relates to the field of lubrication, more particularly lubrication in a turbomachine (in particular an aircraft), more particularly still to the monitoring of the lubricating oil.

BACKGROUND

The patent document published EP 3 150 265 A1 discloses a turbomachine oil tank, equipped at the inlet with a rotary deaerator. The air-laden oil arrives laterally at an inlet located at an upper part of the tank. This inlet opens into a cavity housing a rotor configured to be driven by the flow of air-laden oil. The rotation of the rotor throws the oil particles on a side wall of the cavity, these then flowing by gravity towards the reservoir. The air thus separated from the oil particles is evacuated to a vent located above the rotor.

The patent document published FR 2 443 691 A1 discloses a detector for the presence of magnetizable particles in oil, based on a measurement of electrical resistance. A permanent magnet is placed in the detector so as to attract and accumulate the ferromagnetic particles contained in the oil and circulating near the detector. This accumulation of ferromagnetic particles forms an electrically conductive bridge modifying the measured electrical resistance. This detector is intended to be mounted through a lower wall of an oil sump.

The patent document published WO 2007/088015 A1 discloses a detector of ferromagnetic particles in an oil flow circulating in a pipe. The detection principle is based on magnetism with a transmitter coil and a receiver coil, and can only work with ferromagnetic particles. The potentially large oil flow, however, makes detection difficult and potentially uncertain.

The patent document published EP 3 220 168 A1 discloses a detector of ferromagnetic particles in lubricating oil of a turbomachine, based on magnetism with a transmitter coil and a receiver coil, similar to the previous teaching (WO 2007/088015 A1). The detector is designed to be arranged laterally to a pipe in which the lubricating oil circulates. The detector includes a permanent magnet to attract ferromagnetic particles, their accumulation altering the magnetic field measured by the receiver coil.

These various detectors have the disadvantage of only detecting ferromagnetic particles and may fail to detect certain particles, due to a lack of accumulation of these particles by the permanent magnet or by a size and/or a too low concentration to be detected (WO 2007/088015 A1).

SUMMARY

The object of the invention is to overcome at least one of the drawbacks of the aforementioned state of the art. More particularly, the aim of the invention is to improve the detection of particles in the lubricating oil of a turbomachine.

The invention has for object a device for detecting particles in a lubricating oil of a turbomachine, comprising a particle separator; at least one particle detector; remarkable in that the device further comprises a bypass conduit for the oil concentrating the particles, fluidically connected to an oil outlet of the particle separator; and in that the at least one particle detector is operatively mounted on the bypass conduit so as to be able to detect particles in the bypass conduit.

A bracket mechanically supporting the bypass conduit can be provided. It can be rigidly linked to the particle separator.

According to an exemplary advantageous embodiment of the invention, the particle separator comprises an oil settling tank, the oil outlet being a fluidic outlet of the oil settling tank.

According to an exemplary advantageous embodiment of the invention, the particle separator comprises a runoff wall for the oil towards the oil settling tank.

According to an exemplary advantageous embodiment of the invention, the runoff wall is circular and forms a cyclone for a mixture of oil with air.

According to an exemplary advantageous mode of the invention, the particle separator is formed in an air/oil separator.

According to an exemplary advantageous embodiment of the invention, the air/oil separator is of the cyclonic type with an inlet for the air-laden oil, an air outlet and an air-discharged oil outlet, the oil settling tank being fluidly located between the air-laden oil inlet and the air-discharged oil outlet.

According to an exemplary advantageous mode of the invention, the at least one particle detector comprises an optical detector capable of detecting non-ferromagnetic particles.

According to an exemplary advantageous embodiment of the invention, the at least one particle detector comprises at least one magnetic detector capable of detecting ferromagnetic particles.

According to an exemplary advantageous embodiment of the invention, the bypass conduit is a first bypass conduit and the oil outlet of the particle separator is a first oil outlet, the detection device comprising at least a second bypass conduit connected fluidically to a second oil outlet of the particle separator, concentrating the particles, and at least one of the at least one particle detector is operatively mounted on the second bypass conduit so as to be able to detect the particles in the bypass conduit.

According to an exemplary advantageous embodiment of the invention, the oil settling tank is a first oil settling tank, the particle separator comprising a second oil settling tank, the second oil outlet being a fluid outlet of the second oil settling tank.

Advantageously, in various embodiments the bypass conduit(s) each have an average section less than or equal to 700 $mm^2$, in various instances 600 $mm^2$, for example 500 $mm^2$.

Advantageously, in various embodiments the detection device is configured so that the flow of oil in the or each of the bypass conduit(s) has a speed less than or equal to 2 m/s, in various instances 1 m/s, for example 0.5 m/s.

Advantageously, in various embodiments the bypass conduit is separate from the particle separator. Advantageously, in various embodiments the bypass conduit is external to the particle separator. Advantageously, in various embodiments the bypass conduit comprises a separate fluid outlet from the particle separator so as to be able to be connected to a main flow from the particle separator to an enclosure, or directly to the enclosure. Advantageously, in various embodiments the bypass conduit forms a U-shaped loop.

The invention also relates to a lubricating oil reservoir for a lubricating system of a turbomachine, in particular an aircraft, comprising: an enclosure for the lubricating oil; a device for detecting particles in the lubricating oil, arranged upstream of the enclosure for the lubricating oil; remarkable in that the detection device is according to the invention.

According to an exemplary advantageous embodiment of the invention, the particle separator is at a distance from the enclosure, a conduit fluidically connecting the particle separator to the enclosure.

According to an exemplary advantageous embodiment of the invention, the detection device is rigidly fixed to the enclosure by a support.

According to an advantageous mode of the invention, the particle separator is integrated into the enclosure.

Advantageously, in various embodiments the bypass conduit joins the main oil flow from the particle separator to the enclosure, or the enclosure directly.

Advantageously, in various embodiments the particle detection device is located at an upper part of the enclosure, in various instances above the enclosure.

The invention also relates to a lubrication system for a turbomachine, in particular for an aircraft, comprising conduits for supplying and returning lubricating oil; at least one lubricating oil circulation pump in the conduits; a lubricating oil reservoir fluidly connected to the conduits and to the at least one pump; remarkable in that the lubricating oil reservoir is according to the invention.

The invention also relates to a turbomachine, in particular for an aircraft, comprising a device for detecting particles in a lubricating oil, characterized in that the detection device is according to the invention.

The invention also relates to a turbine engine comprising a lubricating oil reservoir for a lubrication system, characterized in that the lubricating oil reservoir is according to the invention.

The invention also relates to a turbomachine comprising a lubrication system, characterized in that the lubrication system is according to the invention.

The measures of the invention are advantageous in that they make it possible to achieve better detection of particles in a lubricating oil. Detection is better in that particles are more reliably detected regardless of their morphology.

The morphology of the particles can indeed have a significant impact on their detection. The morphology of the particles can be characterized by the mass/surface ratio, directly dependent on the average diameter in the case of particles close to a spherical shape or on a ratio between the largest dimension and the smallest dimension in the case of particles of non-spherical shape, and also of the density of their material.

The quality of detection depends on the segregation of the particles at the level of the particle separator and also on the quality of their detection in the bypass conduit. The provision of a bypass conduit at the outlet of the particle separator allows the latter to empty gradually and thus avoid accumulation and saturation. The flow in the bypass conduit allows a stabilized and controlled transport of particles with a significantly higher concentration than in the main flow due to a lower flow. Such an approach makes it possible to overcome the difficulties of detecting particles of particular morphologies, such as in particular with low mass/surface ratios.

The bypass conduit is also advantageous in that it makes it possible to provide several particle detectors in series along the duct in question. This means that the segregation of particles by the particle separator and their movement at controlled speed and at higher concentration are used for these several particle detectors.

The fact of being able to provide several particle detectors makes it possible, at low additional cost, to detect different materials, such as in particular non-ferromagnetic materials and non-metallic materials. It is in fact now common to provide rolling bearings or bearings made of ceramic material, capable of producing particles of ceramic material.

DRAWINGS

DETAILED DESCRIPTION

Figure 1:
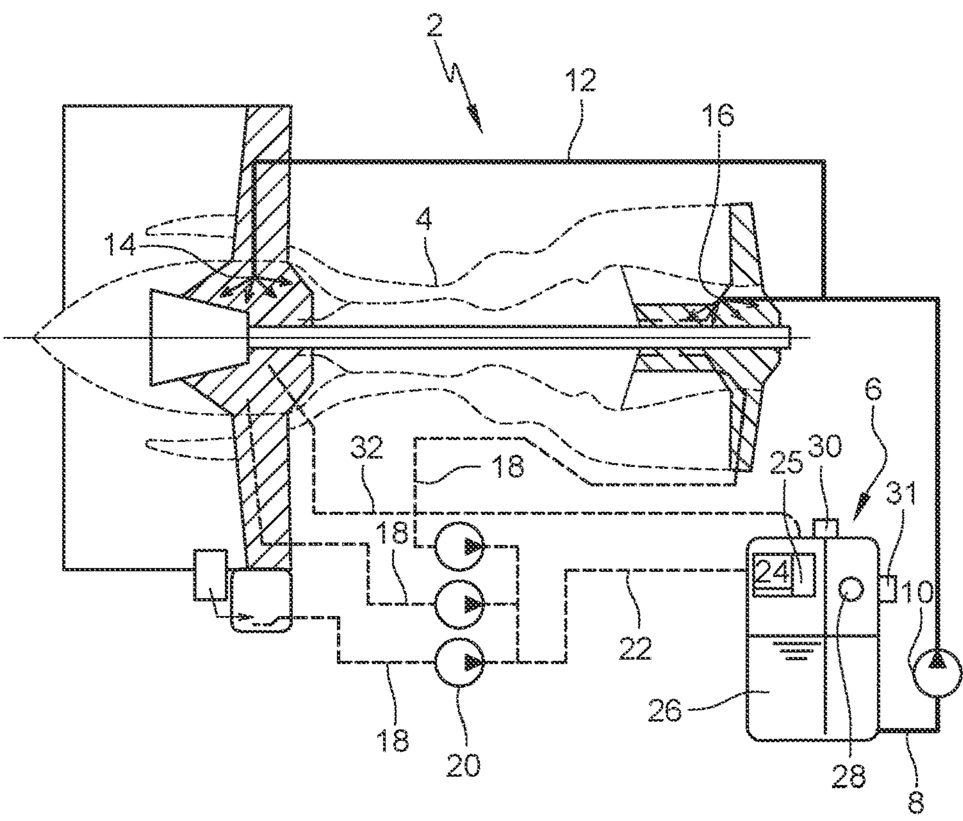
FIG. 1 is an exemplary schematic view in longitudinal couple of a turbine engine, illustrating the lubrication system of the turbine engine, in accordance with various embodiment of the invention.

In FIG. 1 is illustrated a lubrication system of an aircraft engine 4. The lubrication system 2 essentially comprises an oil reservoir 6, an outlet conduit 8 connected to a supply pump 10. Conduits 12 convey the oil displaced by the lubricating pump to various enclosures of bearings to be lubricated 14 and 16 at the front and rear parts of the engine 4. The oil is then recovered at the bottom of these enclosures by recovery conduits 18 as well as by a or recovery pumps 20. This air-laden oil is then rerouted via the conduit 22 to reservoir 6. The latter comprises an enclosure 26 with an air/oil separator 24 disposed at an upper part of enclosure 26 and connected to the oil return pipe 22. The reservoir 6 can also include a window 28 for visual inspection of the normal level, a level detector 30 as well as an additional level detector 31. The upper part of the enclosure 26 of the reservoir 6 is also connected via a pipe 32 to one or more enclosures 14 and 16 of the engine, and this, in order to allow the evacuation of the air from the recovery pumps, this air then being separated from the oil.

The supply and recovery pumps 10 and 20 are in various instances of the volumetric type and driven by the main shaft of the motor. When the engine is stopped, the oil present in the lubrication enclosures and the supply and recovery lines returns to reservoir 6.

The air/oil separator 24 is coupled to a device 25 for detecting particles in the oil.

Figure 2:
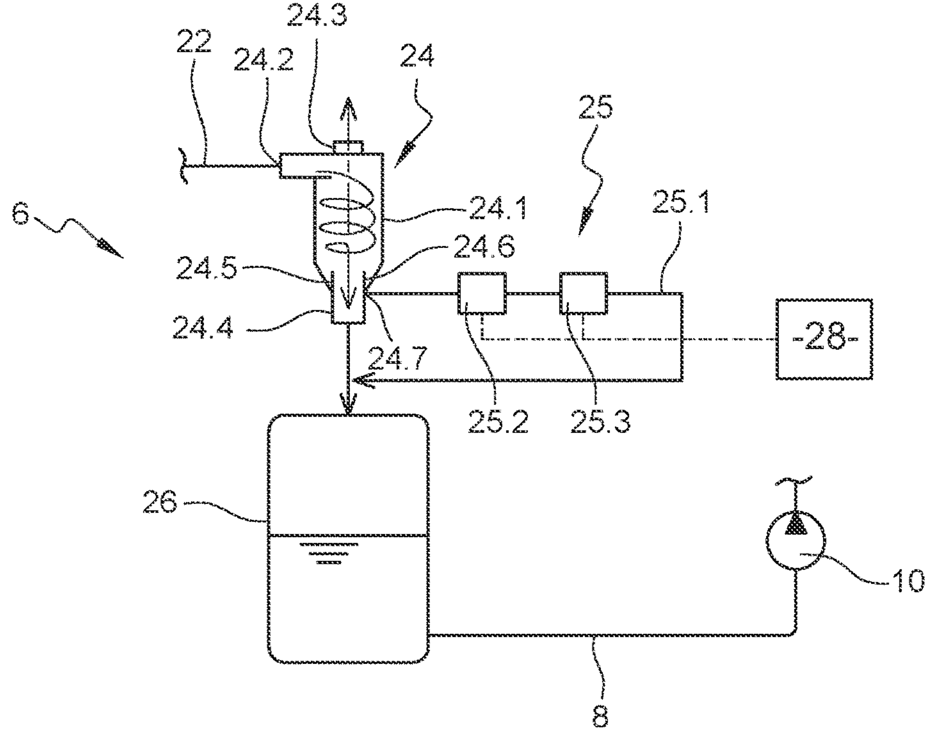
FIG. 2 is an exemplary hydraulic representation of the reservoir part of the lubrication system of FIG. 1, detailing a device for detecting particles in a lubricating oil according to various embodiments of the invention.

FIG. 2 exemplarily details the reservoir part of the lubrication circuit of FIG. 1, in particular the device 25 for detecting particles in the oil.

The air/oil separator 24 is in this case of the cyclonic type, namely configured to form a cyclone with the flow of air-laden oil in order to project the oil particles against a circular wall and to guide and separate the air thus discharged of oil particles. More particularly to the air/oil separator 24 of FIG. 2, the latter comprises a closed circular wall 24.1, in this case generally cylindrical, with a side inlet 24.2 for the flow of air-laden oil conveyed by the pipe 22, an outlet, in this case central, for air separated from the oil 24.3 and an outlet, in this case central, for oil separated from the air 24.4. The air 24.3 and oil 24.4 outlets are opposed along the longitudinal axis of the circular wall 24.1. The oil outlet 24.4 is located at a low level in order to be able to collect the oil separated from the air by gravity, the latter flowing along the circular wall 24.1. The air outlet 24.3 is located at an opposite high level.

The circular wall 24.1 advantageously has a conical profile at a lower part adjacent to the central oil outlet 24.4. The air/oil separator 24 comprises an internal wall 24.5 forming with the circular wall 24.1 an oil settling tank 24.6 for the oil separated from the air and flowing along the circular wall 24.1. This tank is particularly interesting in that it allows the particles contained in the oil to accumulate in the oil settling tank 24.6 while allowing the oil to flow, by overflow, towards the enclosure 26 of the reservoir, via the central oil outlet 24.4.

The device 25 for detecting particles in the lubricating oil comprises a bypass conduit 25.1 fluidly connected to an outlet 24.7 of the oil settling tank 24.6 so as to form a reduced oil flow parallel to the main oil flow from the air/oil separator 24 towards the enclosure 26 of the reservoir. The bypass conduit 25.1 joins the main oil flow or directly the enclosure 26. The device 25 for detecting particles in the lubricating oil also comprises one or more particle detectors 25.2 and 25.3. Each of these detectors is coupled operationally to the bypass conduit 25.1 so as to detect any particles contained in the oil circulating in the bypass conduit 25.1.

The particle detector(s) can be of different types. A first type can be for detecting metallic particles, such as for example the detectors marketed under the name Metallscan®, in particular of the MS1000 series, by the company Gastops®, or even under the name QDM® by the company Eaton®. A second type can be for detecting non-metallic particles, such as optical or vibration detectors.

The particle detectors 25.2 and 25.3 are advantageously electrically connected to a control and/or evaluation unit 28 making it possible to produce structured information as to the presence of particles in the oil, such as in particular the nature of the particles (metallic, non-metallic), their concentration and/or quantity (for example by mass).

The oil flow in the bypass conduit 25.1 is lower than the main flow from the air/oil separator 24 to the enclosure 26 of the reservoir. This flow can be produced by gravity and/or by means of a pump (not shown) arranged, for example, in a fluidic manner, in the bypass conduit 25.1. It can be a low-flow pump, such as a metering pump, for example.

The reduced flow along the bypass conduit 25.1 is particularly favorable to the detection of particles, whether metallic or non-metallic. A reduced section, compared to a main duct, of the bypass conduit 25.1 and a limited speed of movement within the conduit in question allows each of the particle detectors to be active at the detection level over all or almost all of the section of the bypass conduit 25.1 and to detect with greater reliability any particle circulating in the bypass conduit 25.1. The average passage section of the bypass conduit 25.1 is advantageously less than or equal to 700 $mm^2$, 600 $mm^2$ or even 500 $mm^2$. The speed of movement of the oil in the bypass conduit 25.1 is advantageously less than or equal to 2 m/s, 1 m/s or even 0.5 m/s.

Figure 3:
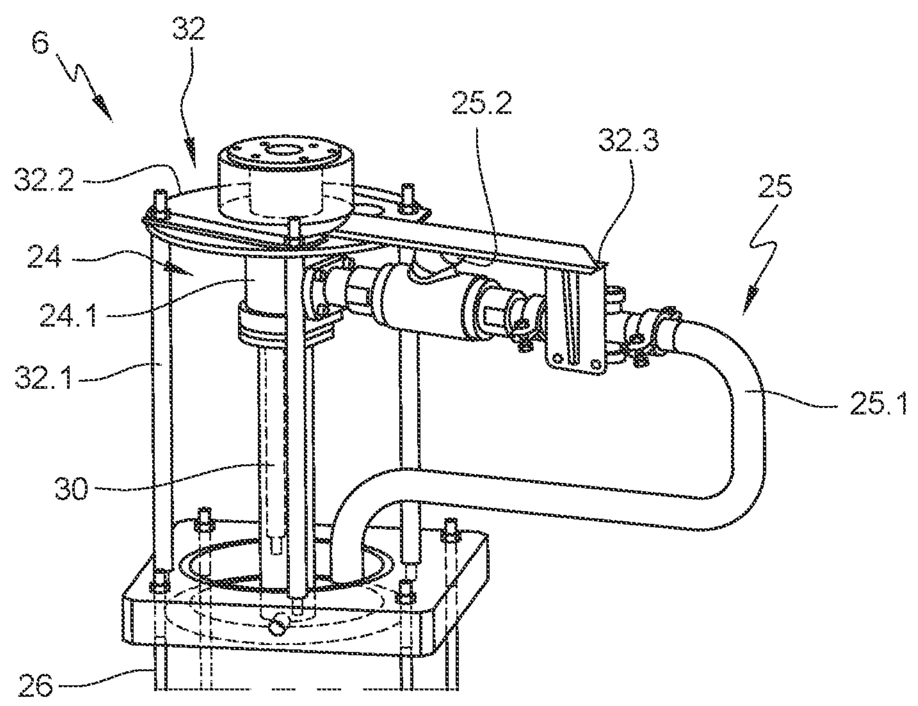
FIG. 3 is an exemplary perspective view of an air/oil separator with a particle detection device, as shown schematically in FIG. 2, in accordance with various embodiment of the invention.

FIG. 3 is a perspective view of an air/oil separator with a particle detection device, as shown schematically in FIG. 2.

It can be observed that the air/oil separator 24 is rigidly fixed to the enclosure 26 by means of a support 32. The latter comprises rods 32.1 rigidly fixed to an upper plate of the enclosure 26. At the distal ends of these rods is fixed a plate 32.2 of the support 32. The air/oil separator 24 is fixed to the plate 32.3 of the support 32.

The support 32 also comprises an arm 32.3 extending essentially radially with respect to a longitudinal axis of the reservoir 6, configured to support the bypass conduit 25.1 of the particle detection device 25. In this case the arm 32.3 extends from plate 32.2. It includes a flange for fixing a bypass conduit 25.1 connection. In this case, a single particle detector 25.2 is present. It is placed between the fixing flange of the arm 32.3 and the circular wall 24.1 of the air/oil separator 24.

One can also observe the duct 30 connecting the central oil outlet of the air/oil separator 24 and the enclosure 26. It extends essentially longitudinally in a central position with respect to the enclosure 26.

Figure 4:
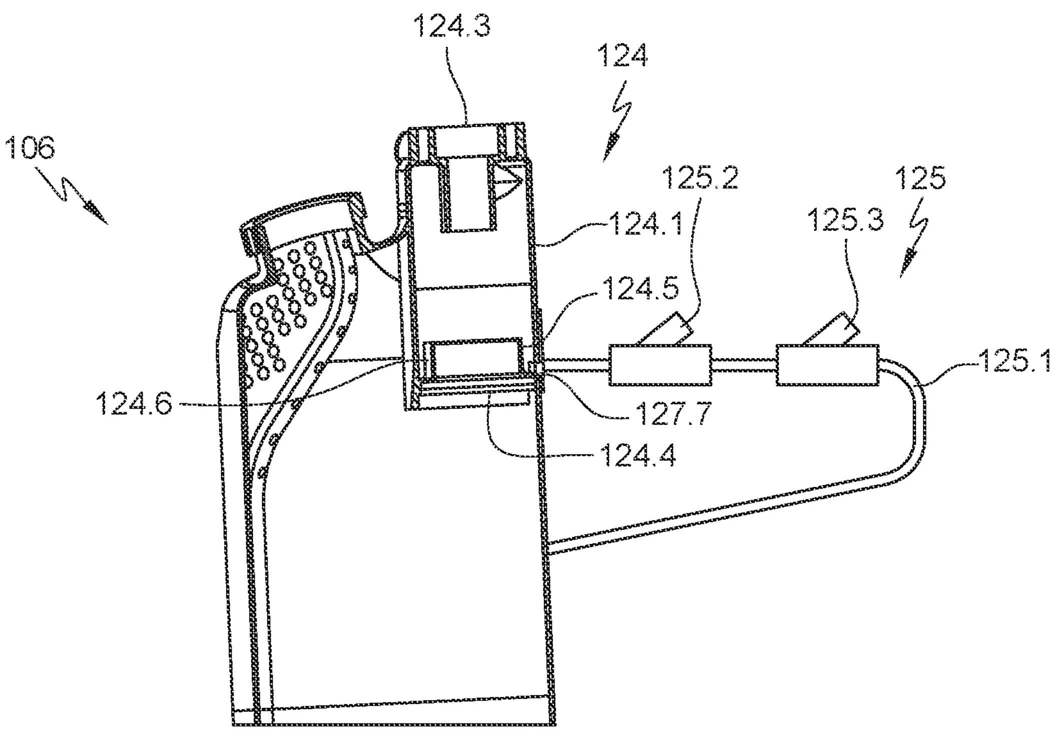
FIG. 4 is an exemplary sectional view of an air/oil separator with a particle detection device, as shown schematically in FIG. 2, integrated into a turbomachine lubricating oil reservoir, in accordance with various embodiment of the invention.

FIG. 4 is a sectional view of an air/oil separator with a particle detection device, as shown schematically in FIG. 2, integrated into the enclosure of the turbomachine lubricating oil reservoir. The reference numbers of FIGS. 1 to 3 are used to designate the same elements, these numbers being however increased by 100. Reference is also made to the description of these elements in relation to FIGS. 1 to 3.

It can be observed that the circular wall 124.1 of the air/oil separator 124 is partially integrated into the wall of the enclosure 126 of the reservoir 106. The oil outlet 124.4 then opens directly into the enclosure 126 without necessarily passing through a conduit or pipe.

It can also be observed that the circular wall 124.1 is generally cylindrical without having a conical lower portion as in FIG. 2. The bottom of the settling tank 124.6 is then generally flat and annular around the internal wall 124.5 delimiting the settling tank 124.6.

The device 125 for detecting particles in the lubricating oil comprises, similarly to FIG. 2, the bypass conduit 125.1 fluidly connected to the settling tank 124.6 so as to form a reduced oil flow parallel to the main oil flow main oil from air/oil separator 124 to the enclosure 126 of the reservoir.

In general, it is conceivable to provide several bypass conduits connected fluidically to the same lubrication circuit, more particularly to the same oil reservoir or even to the same air/oil separator. The particle separator then comprises several outlets, each of which is connected to one of the bypass conduits, respectively. The multiple outlets of the particle separator can then be configured to separate different types and/or sizes of particles. Each bypass conduit can then be configured to specifically detect one of these types and/or one of these sizes of particles. In the case where the particle separator is formed by an air/oil separator of the cyclonic type with an oil runoff wall, this wall can comprise several outlets at different levels along the longitudinal direction of the wall. Different oil settling tanks can then be provided on the wall in question, at different levels so as to retain and therefore separate the particles specifically projected against the wall between this level and the upper adjacent level.

What is claimed is:

1. A device for detecting particles in a lubricating oil of a turbomachine, said device comprising:

a particle separator comprising a circular runoff wall for oil;

a bypass conduit for the oil concentrating the particles, separate from the particle separator and fluidly connected to an oil outlet of the particle separator so as to be able to form a reduced oil flow parallel to a main oil flow, concentrating the particles; and at least two particle detectors operatively mounted on the bypass conduit so as to be able to detect particles in the bypass conduit, the at least two particle detectors being arranged in series along the bypass conduit;

wherein the particle separator comprises an internal wall and an oil settling tank delimited by the circular wall and said internal wall, the oil outlet being a fluid outlet of the oil settling tank;

wherein the circular runoff wall extends, from an oil inlet to the oil outlet, continuously with a constant diameter, or with a decreasing diameter inwardly toward the internal wall;

wherein an average flow passage cross-sectional area of the bypass conduit is less than or equal to 700 $mm^2$;

wherein the device is configured such that a flow velocity of the oil in the bypass conduit is less than or equal to 2 m/s;

wherein the bypass conduit forms a U-shaped loop; and wherein the bypass conduit comprises a low-flow metering pump arranged in said bypass conduit and configured to produce the reduced oil flow.

2. The detection device according to claim 1, wherein the circular runoff wall directs the oil towards the oil settling tank.

3. The detection device according to claim 2, wherein the circular runoff wall forms a cyclone for mixing oil with air.

4. The detection device according to claim 1, wherein the particle separator is formed in an air/oil separator.

5. The detection device according to claim 4, wherein the air/oil separator is of a cyclonic type with the inlet for air-laden oil, an air outlet and an outlet for air-discharged oil, the oil settling tank being located fluidically between the inlet for air-laden oil and the outlet for air-discharged oil.

6. The detection device according to claim 1, wherein the at least one particle detector comprises an optical detector capable of detecting non-ferromagnetic particles.

7. The detection device according to claim 1, wherein the at least one particle detector comprises at least one magnetic detector capable of detecting ferromagnetic particles.

8. The detection device according to claim 1, wherein the internal wall extends longitudinally outwardly by a height greater than the longitudinal height of the oil outlet of the oil settling tank, such that the oil outlet is positioned below an upper edge of the internal wall so as to enable overflow of oil and retention of heavier particles at the bottom of the oil settling tank.

9. A lubricating oil reservoir for a turbomachine lubrication system, said lubricating oil reservoir comprising:

an enclosure for lubricating oil;

a device for detecting particles in the lubricating oil, arranged upstream of the enclosure for the lubricating oil;

wherein the detection device comprises:

a particle separator comprising a circular runoff wall for oil;

a bypass conduit for the oil concentrating the particles, separate from the particle separator and fluidly connected to an oil outlet of the particle separator so as to be able to form a reduced oil flow parallel to a main oil flow, concentrating the particles; and at least two particle detectors operatively mounted on the bypass conduit so as to be able to detect particles in the bypass conduit, the at least two particle detectors being arranged in series along the bypass conduit;

wherein the particle separator comprises an internal wall and an oil settling tank delimited by the circular runoff wall and said internal wall, the oil outlet being a fluid outlet of the oil settling tank;

wherein the circular runoff wall extends, from an oil inlet to the oil outlet, continuously with a constant diameter, or with a decreasing diameter inwardly toward the internal wall;

wherein an average flow passage cross-sectional area of the bypass conduit is less than or equal to 700 $mm^2$;

wherein the device is configured such that a flow velocity of the oil in the bypass conduit is less than or equal to 2 m/s;

wherein the bypass conduit forms a U-shaped loop; and wherein the bypass conduit comprises a low-flow metering pump arranged in said bypass conduit and configured to produce the reduced oil flow.

10. The lubricating oil reservoir according to claim 9, wherein the particle separator is remote from the enclosure, a duct fluidly connecting the particle separator to the enclosure.

11. The lubricating oil reservoir according to claim 10, wherein the detection device is rigidly attached to the enclosure by a bracket.

12. The lubricating oil reservoir according to claim 9, wherein the particle separator is integrated into the enclosure.

13. The lubricating oil reservoir according to claim 9, wherein the bypass conduit joins the main oil flow from the particle separator to the enclosure, or directly to the enclosure.

14. A turbomachine lubrication system, said turbomachine comprising:

conduits for supplying and returning lubricating oil;

at least one circulation pump for lubricating oil in the conduits;

a lubricating oil reservoir fluidly connected to the conduits and to the at least one circulation pump;

wherein the lubricating oil reservoir comprises:

an enclosure for the lubricating oil;

a device for detecting particles in the lubricating oil, arranged upstream of the enclosure for the lubricating oil;

wherein the detection device comprises:

a particle separator comprising a circular runoff wall for oil;

a bypass conduit for the oil concentrating the particles, separate from the particle separator and fluidly connected to an oil outlet of the particle separator so as to be able to form a reduced oil flow parallel to a main oil flow, concentrating the particles; and at least two particle detectors operatively mounted on the bypass conduit so as to be able to detect particles in the bypass conduit, the at least two particle detectors being arranged in series along the bypass conduit;

wherein the particle separator comprises an internal wall and an oil settling tank delimited by the circular runoff wall and said internal wall, the oil outlet being a fluid outlet of the oil settling tank;

wherein the circular runoff wall extends, from an oil inlet to the oil outlet, continuously with a constant diameter, or with a decreasing diameter inwardly toward the internal wall;

wherein an average flow passage cross-sectional area of the bypass conduit is less than or equal to 700 $mm^2$;

wherein the device is configured such that a flow velocity of the oil in the bypass conduit is less than or equal to 2 m/s;

wherein the bypass conduit forms a U-shaped loop; and wherein the bypass conduit comprises a low-flow metering pump arranged in said bypass conduit and configured to produce the reduced oil flow.

15. A turbomachine comprising a device for detecting particles in a lubricating oil, wherein the detection device comprises:

a particle separator comprising a circular runoff wall for oil;

a bypass conduit for the oil concentrating the particles, separate from the particle separator and fluidly connected to an oil outlet of the particle separator so as to be able to form a reduced oil flow parallel to a main oil flow, concentrating the particles; and at least two particle detectors operatively mounted on the bypass conduit so as to be able to detect particles in the bypass conduit, the at least two particle detectors being arranged in series along the bypass conduit;

wherein the particle separator comprises an internal wall and an oil settling tank delimited by the circular runoff wall and said internal wall, the oil outlet being a fluid outlet of the oil settling tank;

wherein the circular runoff wall extends, from an oil inlet to the oil outlet, continuously with a constant diameter, or with a decreasing diameter inwardly toward the internal wall;

wherein an average flow passage cross-sectional area of the bypass conduit is less than or equal to 700 $mm^2$;

wherein the device is configured such that a flow velocity of the oil in the bypass conduit is less than or equal to 2 m/s;

wherein the bypass conduit forms a U-shaped loop; and wherein the bypass conduit comprises a low-flow metering pump arranged in said bypass conduit and configured to produce the reduced oil flow.

* * * * *